(12) United States Patent
Ozaki et al.

(10) Patent No.: US 10,799,362 B2
(45) Date of Patent: Oct. 13, 2020

(54) AORTIC VALVE RECONSTRUCTION TRAINING KIT

(71) Applicant: JAPANESE ORGANIZATION FOR MEDICAL DEVICE DEVELOPMENT, INC., Tokyo (JP)

(72) Inventors: Shigeyuki Ozaki, Tokyo (JP); Takahiro Uchida, Tokyo (JP)

(73) Assignee: JAPANESE ORGANIZATION FOR MEDICAL DEVICE DEVELOPMENT, INC., Tokyo (JP)

( * ) Notice: Subject to any disclaimer, the term of this patent is extended or adjusted under 35 U.S.C. 154(b) by 159 days.

(21) Appl. No.: 15/807,231

(22) Filed: Nov. 8, 2017

(65) Prior Publication Data
US 2018/0098852 A1     Apr. 12, 2018

Related U.S. Application Data

(63) Continuation of application No. PCT/JP2016/063347, filed on Apr. 28, 2016.

(51) Int. Cl.
*G09B 23/28* (2006.01)
*A61F 2/24* (2006.01)
(Continued)

(52) U.S. Cl.
CPC .............. *A61F 2/2496* (2013.01); *A61F 2/06* (2013.01); *A61F 2/24* (2013.01); *A61F 2/76* (2013.01);
(Continued)

(58) Field of Classification Search
USPC .................. 434/262, 267, 268, 272
See application file for complete search history.

(56) References Cited

U.S. PATENT DOCUMENTS

| | | | |
|---|---|---|---|
| 5,716,370 A | 2/1998 | Williamson, IV et al. | |
| 6,062,866 A | * 5/2000 | Prom | G09B 23/28 434/268 |

(Continued)

FOREIGN PATENT DOCUMENTS

| | | |
|---|---|---|
| JP | 550477 U | 7/1993 |
| JP | 2009077838 A | 4/2009 |

(Continued)

OTHER PUBLICATIONS

International Search Report for corresponding International Application No. PCT/JP2016/063347, dated Aug. 2, 2016.

*Primary Examiner* — Kurt Fernstrom
(74) *Attorney, Agent, or Firm* — Myers Wolin, LLC

(57) ABSTRACT

A training kit is provided for practicing aortic valve reconstruction. The aortic valve reconstruction training kit is provided with a blood vessel model and multiple valve leaflet models, and the blood vessel model has a base-capped or base-uncapped cylindrical form having an opening formed on at least the top part thereof. The blood vessel model also has a valve ring part which is formed in the middle of the cylinder and to which the valve leaflet models can be sutured. By using the training kit, it becomes possible to practice a suturing technique that is believed to be the most difficult in aortic valve reconstruction, namely, a technique of accurately suturing a new valve leaflet to a valve ring part, to which an abnormal valve leaflet has been attached, of a cylindrical aorta while viewing the inside of the aorta from above.

8 Claims, 10 Drawing Sheets

(51) Int. Cl.
*A61F 2/76* (2006.01)
*A61F 2/06* (2013.01)
*A61L 27/00* (2006.01)
*G09B 23/34* (2006.01)
*G09B 23/32* (2006.01)
*G09B 23/30* (2006.01)

(52) U.S. Cl.
CPC .............. *A61L 27/00* (2013.01); *G09B 23/28* (2013.01); *G09B 23/30* (2013.01); *G09B 23/32* (2013.01); *G09B 23/34* (2013.01); *A61F 2/2463* (2013.01); *A61F 2/2472* (2013.01)

(56) References Cited

U.S. PATENT DOCUMENTS

| | | | |
|---|---|---|---|
| 6,338,740 B1 | 1/2002 | Carpentier | |
| 6,511,325 B1* | 1/2003 | Lalka | A61B 8/587 |
| | | | 434/267 |
| 7,083,418 B2* | 8/2006 | Baldauf | G09B 23/34 |
| | | | 434/267 |
| 7,238,200 B2* | 7/2007 | Lee | A61F 2/2412 |
| | | | 623/2.14 |
| 8,021,161 B2* | 9/2011 | LaFrance | G09B 23/32 |
| | | | 434/262 |
| 9,155,617 B2* | 10/2015 | Carpentier | A61F 2/2409 |
| 9,539,094 B2* | 1/2017 | Dale | A61B 17/00234 |
| 2003/0078651 A1 | 4/2003 | Schoon | |
| 2006/0095125 A1* | 5/2006 | Chinn | A61F 2/2409 |
| | | | 623/2.4 |
| 2007/0218437 A1 | 9/2007 | Lotano et al. | |
| 2011/0251598 A1 | 10/2011 | Ozaki | |
| 2012/0288840 A1* | 11/2012 | Gurdin | G09B 23/30 |
| | | | 434/272 |
| 2013/0295541 A1* | 11/2013 | Alkhatib | G09B 23/30 |
| | | | 434/267 |
| 2014/0272867 A1* | 9/2014 | Ratcliffe | G09B 23/28 |
| | | | 434/262 |
| 2015/0088247 A1 | 3/2015 | L'Heureux et al. | |
| 2016/0027345 A1* | 1/2016 | Carson | G09B 23/288 |
| | | | 434/262 |

FOREIGN PATENT DOCUMENTS

| | | |
|---|---|---|
| JP | 201232457 A | 2/2012 |
| JP | 201268505 A | 4/2012 |
| JP | 5106019 B2 | 10/2012 |
| JP | 2013029820 A | 2/2013 |

* cited by examiner (a)

(b)

AORTIC VALVE RECONSTRUCTION TRAINING KIT

CROSS REFERENCES TO RELATED APPLICATIONS

The present application is a continuation under 35 U.S.C. § 120 of International Application PCT/JP2016/063347, filed Apr. 28, 2016, which claims priority to Japanese Patent Application No. 2015-095322 2015, filed May 8, 2015, the contents of each of which are incorporated herein by reference.

TECHNICAL FIELD

The present invention relates to a training kit that can be used to practice an aortic valve reconstruction surgery.

BACKGROUND ART

The heart acts as a pump that pumps blood to the entire body through the aorta. Here, for example, a heart valve (aortic valve) formed at an outlet through which blood flows out from the left ventricle of the heart to the aorta consists of three saucer-shaped valve leaflets, each of which is formed of a thin film. When the fluid pressure of blood flow is low, inner membranes of the valve leaflets come together and the heart valve closes, so that the blood flow is blocked. On the other hand, when the fluid pressure of blood flow is high, the inner membranes of the valve leaflets separate from each other and the heart valve opens, so that the blood flows from the heart to the aorta. Each valve leaflet is integrated with the inner wall of the aorta at commissure portions corresponding to both left and right ends of the valve leaflet.

Incidentally, when arteriosclerosis or the like progresses with age, a phenomenon occurs where calcium is attached to the valve leaflet and the valve leaflet becomes calcified and hardened. Thereby, the motion of the valve leaflet is restricted and is not fully opened, so that a disease called as aortic valve stenosis is caused. As a result, the wall of the left ventricle is thickened and enlarged. When the wall of the heart muscle is excessively thickened, results in a shortage of nutrition and oxygen in the blood flow supplied through the coronary artery, causing myocardial ischemia (a state of shortage of nutrition and oxygen). In particular, if the myocardial ischemia occurs for example, during exercise in which demand for oxygen is high, it could cause a risk of symptoms, such cheat pain and syncope.

Here, as a medical treatment for such diseases, as a result of diligent research, the inventors have established an aortic valve reconstruction surgery in place of conventional valve replacement surgery. The aortic valve reconstruction surgery is a surgery that resects only a valve leaflet that has become unusable from among valve leaflets that have been hardened due to deposition of calcium, and replaces the resected valve leaflet with an aortic valve formed from a patient's own biological membrane to restore the valve leaflet while leaving hardened valve leaflets that can be used as valve leaflets by removing calcium. By forming a valve leaflet from a patient's own pericardium or the like and using the valve leaflet as a new aortic valve in this way, it is possible to avoid a problem to cause immunological rejection, a problem to cause blood-clotting reaction (blood clot), and the like. Further, it is not necessary to purchase an expensive prosthetic valve. However, in the aortic valve reconstruction surgery, it is necessary to cut out a valve leaflet that matches the thickness of the patient's aorta from a flat pericardium, and it is a problem how to determine the size of valve leaflet that matches the thickness of the patient's aorta.

Therefore, the inventors of the present invention have developed a valve leaflet forming instrument for correctly measuring the size of the patient's valve leaflet and forming a valve leaflet that matches the thickness of the patient's aorta (Patent Literature 1). In the Patent Literature 1, a valve leaflet forming instrument used for the aortic valve reconstruction surgery is disclosed. Specifically, the valve leaflet forming instrument is medically used for treating a valve leaflet abnormality disease by resecting an abnormal valve leaflet of a tricuspid type heart valve or a bicuspid type heart valve of an aortic valve or the like and sutures a valve leaflet formed of an artificial membrane or a biological membrane to a resected portion to reproduce a heart valve. The valve leaflet forming instrument has a plurality of valve leaflet sizers and a template. The valve leaflet sizer is an instrument for determining a valve leaflet size according to the size of the heart valve. The valve leaflet sizer has a structure in which a plurality of sizer blocks having different sizes that measure a length from one commissure portion of a resected valve leaflet to the other commissure portion are attached to handle tips, respectively. Further, an arc surface formed by cutting circular columns having different diameters in an angle according to a central angle of the commissure portion is formed in each sizer block. On the other hand, the template is an auxiliary tool for drawing a valve-leaflet-shaped line on an artificial membrane or a biological membrane according to a measured valve leaflet size. When the valve leaflet sizer is inserted into a valve annulus portion where a valve leaflet is resected and both end portions of the arc surface of the sizer block correspond to both commissure portions of the resected valve leaflet, the diameter of a circular column that forms the arc surface of the sizer block is defined as a nominal diameter. In the template, a substantially semi-circular shaped valve leaflet base portion forming portion whose diameter is a sum of the nominal diameter and a margin to suture and a line drawing portion formed of a coaptation zone forming portion connected to the valve leaflet base portion forming portion are formed.

In this way, in a state in which one abnormal valve leaflet of a heart valve such as the aortic valve is resected, the valve leaflet sizer is inserted into the valve annulus portion. At this time, a diameter of the sizer block, of which both end portions of the arc surface correspond to the both commissure portions of the resected valve leaflet, is defined as the nominal diameter, and the nominal diameter can be used as an index to determine the size of the valve leaflet. Further, in the template, the line drawing portion according to the nominal diameter of the sizer block is formed. Therefore, it is possible to form a valve leaflet having a shape according to a shape of the resected valve leaflet by, for example, extending a biological membrane such as a pericardium, pressing the template onto the biological membrane, drawing a valve-leaflet-shaped line along the line drawing portion by a sterilized surgical skin marker or the like, and then cutting the biological membrane along the line. When the cut-out valve leaflet is directly sutured to the valve annulus portion to which the abnormal valve leaflet had been attached, it is possible to form a tricuspid type heart valve such as the aortic valve without, contracting the valve annulus.

CITATION LIST

Patent Literature

Patent Literature 1: JP 5106019 B2

SUMMARY OF INVENTION

Technical Problem

The aortic valve reconstruction surgery is an innovative surgical technique for aortic valve stenosis and aortic valve incompetence. As compared with an aortic valve replacement surgery such as a thoracotomy prosthetic valve replacement surgery using a conventional mechanical valve or biological valve, the aortic valve reconstruction surgery has advantages such as excellent compatibility with a living body, low economic burden, and simplicity in life after the surgery. However, the aortic valve reconstruction surgery requires a special suturing method when suturing a valve leaflet formed of an artificial membrane or a biological membrane to the valve annulus portion of the aorta. In other words, it is necessary for an operator to correctly suture a new valve leaflet to a valve annulus portion to which an abnormal valve leaflet has been attached while looking down into the inside of a cylindrical aorta from above. Because the aortic valve reconstruction surgery is not yet widespread in the world, even among cardiovascular surgeons who have abundant surgery experiences, there are few who have experienced a method of the aortic valve reconstruction surgery.

Therefore, at present, a training kit with which the aortic valve reconstruction surgery can be practiced is required.

Solution to Problem

The present invention relates to a training kit for the aortic valve reconstruction surgery. The training kit of the present invention includes a blood vessel model 10 and a plurality of valve leaflet models 20. Alternatively, the training kit may include, instead of the plurality of valve leaflet models 20, a sheet member 30 from which the plurality of valve leaflet models 20 are cut out. The blood vessel model 10 has a bottomed cylindrical shape or a bottomless cylindrical shape where an opening portion 11 is formed at least at an upper portion thereof. Further, the blood vessel model 10 has a valve annulus portion 12, to which the valve leaflet model 20 can be sutured, at around middle of the cylindrical shape.

As in the configuration described above, in the training kit of the present invention, the valve annulus portion 12 is formed in the blood vessel model 10 which has a cylindrical shape (bottomed cylindrical shape or bottomless cylindrical shape) and has the opening portion 11 at an upper portion thereof, and a plurality of valve leaflet models 20 can be sutured to the valve annulus portion 12. Therefore, when using the training kit of the present invention, it is possible to practice a suturing method which is assumed to be the most difficult operation of the aortic valve reconstruction surgery and in which an operator correctly sutures a new valve leaflet to a valve annulus portion of aorta to which an abnormal valve leaflet has been attached while looking down into the cylindrical aorta from above. Moreover, it is possible to cause the operator to perform a simulation close to an actual surgical operation by causing the operator to perform training starting from cutting out a plurality of valve leaflet models 20 from the sheet member 30 simulating a biological membrane. Accordingly, the present invention contributes to the aortic valve reconstruction surgery.

In the training kit of the present invention, it is preferable that the valve annulus portion 12 is formed thick over an entire circumference thereof so as to protrude into the blood vessel model 10.

As in the configuration described above, by forming a raised portion of the valve annulus portion 12 in the blood vessel model 10, it is possible to practice a suturing method in which the operator sutures the valve leaflet model 20 to the valve annulus portion 12 so that the valve leaflet model 20 sags below the valve annulus portion 12. Also in an actual surgical operation, by performing such a suturing method, a natural swelling is formed on the valve leaflet after the suturing and compatibility between the sutured valve leaflet and a living body is improved. Therefore, it is beneficial to practice such a suturing method by using the training kit.

In the training kit of the present invention, it is preferable that the valve annulus portion 12 has a plurality of commissure portions 13 formed at intervals in a circumferential direction of the blood vessel model 10 and the plurality of commissure portions 13 are provided distinguishably from the other regions in the valve annulus portion 12. For example, the commissure portion 13 may be locally thickened and swelled or shown by a hole or a color different from those of the other regions.

As in the configuration described above, by providing a plurality of commissure portions 13 to the valve annulus portion 12 of the blood vessel model 10, it is possible to practice an operation to measure a length between the commissure portions by using a valve leaflet sizer and an operation to suture a valve leaflet with an appropriate size between the commissure portions.

In the training kit according to the present invention, it is preferable that arc lengths of valve annulus portions 12 between the plurality of commissure portions 13 are set to be different from each other.

When all the distances between the commissure portions 13 in the blood vessel model 10 are the same, it is very easy to determine the distances between the commissure portions 13 by using the valve leaflet sizer, so that it is not possible to improve effect of the practice. On the other hand, as in the configuration described above, when the distances between the commissure portions 13 are intentionally differentiated from each other, it is required to measure the distances between the commissure portions 13 by using the valve leaflet sizer for a plurality of times, so that it is possible to efficiently perform training of the aortic valve reconstruction surgery in accordance with an actual clinical use.

In the training kit according to the present invention, it is preferable that the blood vessel model 10 further includes an enlarged diameter portion 14 between the opening portion 11 and the valve annulus portion 12, the enlarged diameter portion 14 having an inner diameter greater than inner diameters of the opening portion 11 and the valve annulus portion 12.

As in the configuration described above, by providing the enlarged diameter portion 14 between the opening portion 11 and the valve annulus portion 12, it is possible to secure a work space for performing work to suture the valve leaflet model 20 to the valve annulus portion 12 by inserting fingers from the opening portion 11. In an actual surgical operation, when a space in front of the valve annulus portion of the aorta is small, an assistant expands the space by using a retractor or the like while the operator performs a suturing operation of a valve leaflet. On the other hand, in the training kit according to the present invention, by forming the enlarged diameter portion 14 in the blood vessel model 10, the assistant who expands the space in front of the valve annulus portion 12 is not required. Therefore, the operator can use the training kit by himself or herself. Further, the operator need not expand the space in front of the valve annulus portion 12 by using the retractor or the like when performing the training, so that the operator can concentrate on the suturing operation of the valve leaflet model 20.

In the training kit of the present invention, it is preferable that the plurality of valve leaflet models 20 are cut out from the sheet member 30 simulating a biological membrane.

As in the configuration described above, by causing the operator to perform training starting from cutting out a plurality of valve leaflet models 20 from the sheet member 30 modeling a biological membrane, it is possible to cause the operator to perform a simulation close to an actual surgical operation.

It is preferable that the training kit of the present invention further includes a pedestal 40 that supports the blood vessel model 10 with the opening portion 11 facing up on a bottom portion side opposite to the opening portion 11 of the blood vessel model 10. Of course, when the blood vessel model 10 stands up independently, the pedestal 40 may not be provided.

As in the configuration described above, by providing the pedestal 40 to a bottom portion of the blood vessel model 10, the blood vessel model 10 can be easily maintained in a substantially upright state. Thereby, it is possible to cause the operator to efficiently perform training of the complicated suturing operation in which the operator correctly sutures a new valve leaflet to the valve annulus portion of aorta to which an abnormal valve leaflet has been attached while looking down into the cylindrical aorta from above.

The training kit of the present invention may further include a photographing unit 50 for photographing the valve annulus portion 12 from the bottom portion side of the blood vessel model 10 in the pedestal 40 or in a cylinder of the blood vessel model 10.

As in the configuration described above, the photographing unit 50 photographs the valve annulus portion 12 from the bottom portion side of the blood vessel model 10, so that it is possible to record a state of operation of suturing the valve leaflet model 20 to the valve annulus portion 12 and present the recorded state of operation to the operator. Thereby, it is possible to efficiently perform the training of the surgical operation.

Advantageous Effects of Invention

According to the training kit of the present invention, it is possible to effectively perform the practice of the aortic valve reconstruction surgery.

DESCRIPTION OF EMBODIMENTS

Hereinafter, embodiments of the present invention will be described with reference to the drawings. The present invention is not limited to the embodiments described below, but includes embodiments appropriately modified from the embodiments described below in a range obvious to those skilled in the art.

[1. Tricuspid Type Training Kit]

Figure 1:
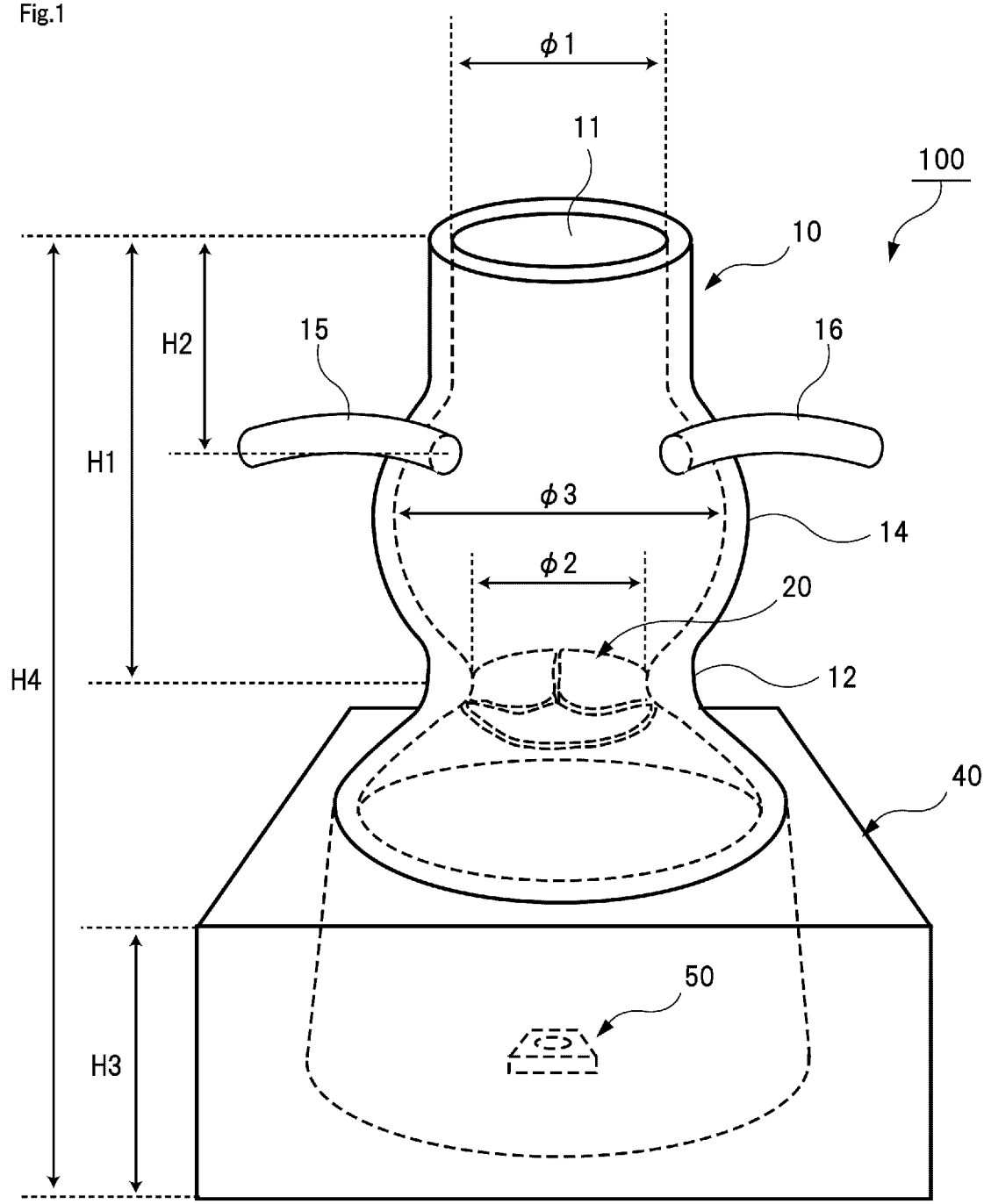
FIG. 1 is a schematic diagram illustrating an entire configuration of a training kit for a tricuspid type heart valve.

FIG. 1 illustrates a training kit 100 for a tricuspid type aortic valve reconstruction surgery. As illustrated in FIG. 1, the training kit 100 includes a blood vessel model 10, a plurality of valve leaflet models 20, and a pedestal 40.

[1-1. Blood Vessel Model]

First, the blood vessel model 10 will be described. The blood vessel model 10 is a model modeled on a human aorta. As illustrated in FIG. 1, the blood vessel model 10 is molded into a cylindrical shape in which a space is formed. The blood vessel model 10 has an opening portion 11 at least in its upper end portion. The blood vessel model 10 only needs to have the upper end opening portion 11, so that the blood vessel model 10 may have a bottomed cylindrical shape in which no opening is formed at a bottom portion opposite to the opening portion 11 or may have a bottomless cylindrical shape in which an opening is also formed at a bottom portion. As illustrated in FIG. 1, an inner diameter φ1 of the opening portion 11 of the blood vessel model 10 is preferable to be 20 mm to 40 mm or 25 mm to 35 mm, and is more preferable to be 28 mm to 32 mm (about 30 mm).

As a material that forms the blood vessel model 10, it is possible to employ a material that is publicly known as a material of a living body model. For example, the blood vessel model 10 can be made of a flexible material (elastomer) such as silicon, urethane, styrene, synthetic rubber, or natural rubber. In addition, the blood vessel model 10 may be made of a flexible material which can maintain its shape and which has elasticity similar to that of living tissue. The blood vessel model 10 has a predetermined thickness. The blood vessel model 10 may be formed of a layer of flexible material or may be formed by laminating a plurality of layers of flexible materials in the thickness direction. When the blood vessel model 10 is formed of a plurality of layers, the quality of material that forms each layer may be different from each other. A plurality of valve leaflet models 20 are sutured to an inner wall of the blood vessel model 10. For example, it is preferable to form the inner wall of the blood vessel model 10 with a relatively soft flexible material and to form an outer wall of the blood vessel model 10 with a relatively hard flexible material. Thereby, it is easy to suture the valve leaflet model 20 to the soft inner wall while maintaining the shape of the blood vessel model 10 by the hard outer wall.

The blood vessel model 10 has a so-called gourd-shape in which, from the upper portion where the opening portion 11 is formed toward a lower portion, there is a portion of which the diameter is the same as that of the opening portion 11 in a certain length of portion, then the inner diameter gradually increases, thereafter the inner diameter gradually decreases, and further thereafter the inner diameter increases. As shown in FIG. 1, in the middle of the blood vessel model 10 in the vertical direction, a portion whose inner diameter is smallest and constricted is a valve annulus portion 12. In FIG. 1, the inner diameter (minimum value) of the valve annulus portion 12 is indicated by reference symbol φ2. It is preferable that the inner diameter φ2 of the valve annulus portion 12 is smaller than the inner diameter φ1 of the opening portion 11 (φ2<φ1). For example, it is preferable that the inner diameter φ2 of the valve annulus portion 12 is 50% to 95% or 60% to 80% of the inner diameter φ1 of the opening portion 11. Specifically, the inner diameter φ2 of the valve annulus portion 12 is preferable to be 10 mm to 30 mm or 15 mm to 25 mm, and is more preferable to be 18 mm to 22 mm (about 20 mm). In FIG. 1, the height from the valve annulus portion 12 to the opening portion 11 is indicated by reference symbol H1. The height H1 from the valve annulus portion 12 to the opening portion 11 may be, for example, 15 mm to 50 mm or 30 mm to 40 mm.

Figure 2:
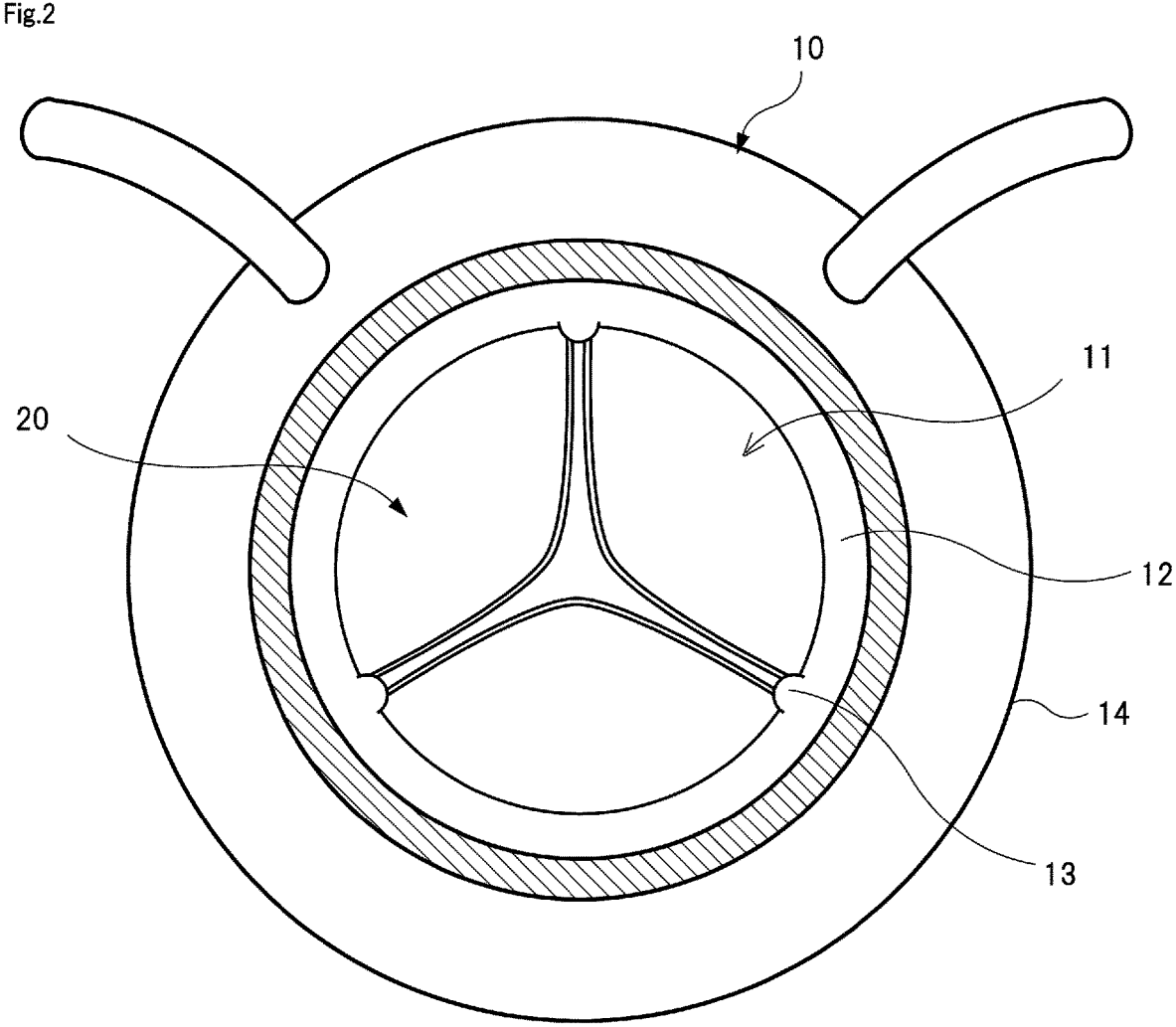
FIG. 2 is a plan view illustrating a blood vessel model as viewed from an upper opening portion.

As shown in FIG. 1, a plurality of valve leaflet models 20 can be sutured to the inner wall of the valve annulus portion 12. FIG. 2 shows a state in which the inside of the blood vessel model 10 is viewed through the opening portion 11. The training kit 100 illustrated in FIGS. 1 and 2 is for training of a tricuspid type aortic valve reconstruction surgery, so that a maximum of three valve leaflet models 20 can be sutured to the inner wall of the valve annulus portion 12 of the blood vessel model 10.

Figure 3:
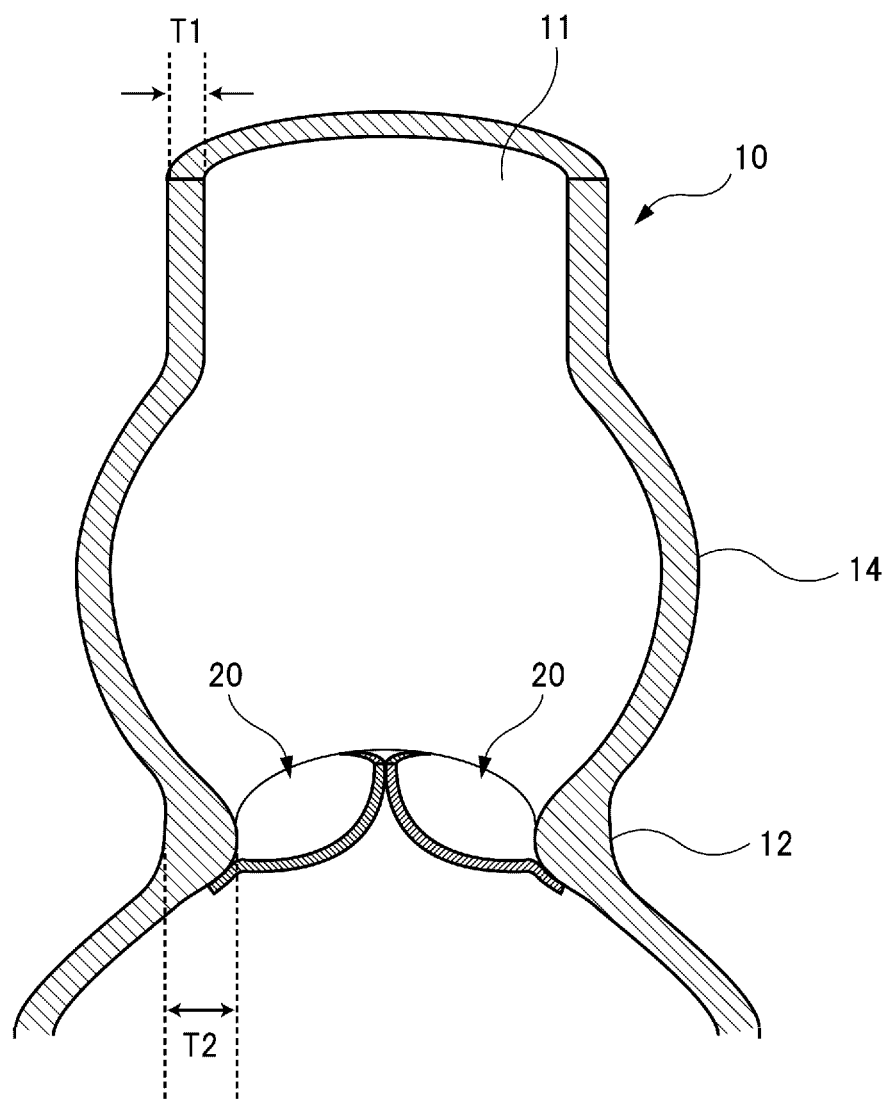
FIG. 3 is a cross-sectional view illustrating an entire structure of the blood vessel model.

FIG. 3 illustrates a vertical cross-sectional view of the blood vessel model 10. As illustrated in FIG. 3, in the valve leaflet model 20, a thickness T2 of the valve annulus portion 12 is formed thicker than a thickness T1 of a normal region. In this way, it is preferable that the valve annulus portion 12 is formed thick over its entire circumference so as to protrude into the blood vessel model 10. Thereby, it is possible to practice a method of suturing the valve leaflet models 20 so that the valve leaflet models 20 sag downward from the valve annulus portion 12. In an actual surgical operation, by performing such a suturing method, a natural swelling is formed in a sutured valve leaflet, so that compatibility between the sutured valve leaflet and a living body is improved. Therefore, it is beneficial to practice such a suturing method by using a training kit. For example, the thickness T2 of the valve annulus portion 12 is preferable to be 110% to 250% or 150% to 200% of the thickness T1 of the normal region. Specifically, the thickness T1 of the normal region of the blood vessel model 10 is preferable to be 0.8 mm to 4 mm or 2 mm to 3 mm. On the other hand, the thickness T2 of the valve annulus portion 12 is preferable to be 2 mm to 6 mm, 2.5 mm to 5.5 mm, or 3 mm to 5 mm.

Figure 4:
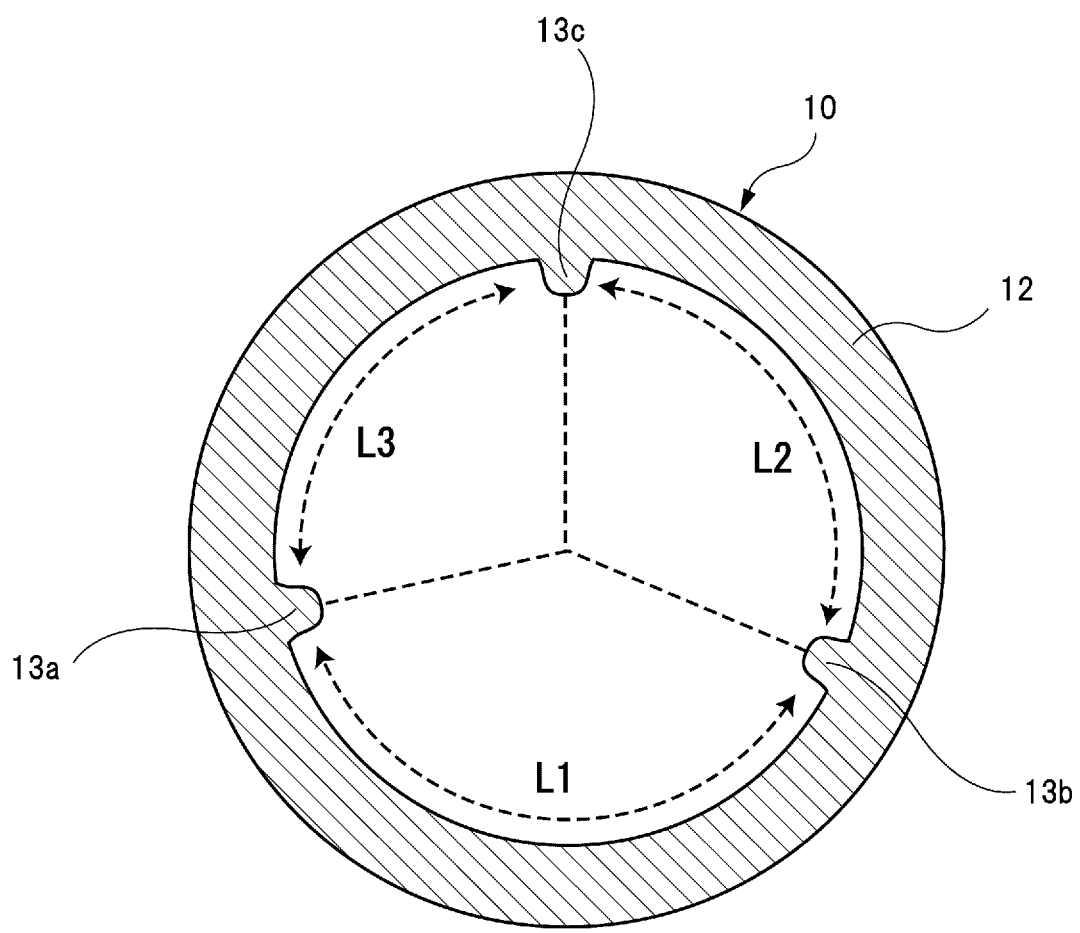
FIG. 4 is a cross-sectional view illustrating a structure of a valve annulus portion of the blood vessel model.

FIG. 4 illustrates a circumferential direction cross-sectional view of the valve annulus portion 12 of the blood vessel model 10. As shown in FIG. 4, a plurality of commissure portions 13 are formed in the valve annulus portion 12 at intervals in the circumferential direction. As the training kit 100 illustrated in FIG. 3 is for training of the tricuspid type aortic valve reconstruction surgery, the commissure portions 13 are formed at three positions. It is only required that the commissure portion 13 is a portion that can be distinguished from the other regions in the valve annulus portion 12. For example, as illustrated in FIG. 4, the commissure portion 13 may be formed thicker than the other regions in the valve annulus portion 12 so as to protrude locally toward the inside of the blood vessel model 10. On the commissure portion 13, a mark may be printed or drawn or may be attached as a seal. Anyway, the commissure portion 13 is shown in a state where an operator can recognize the commissure portion 13 when the operator looks into the valve annulus portion 12 from the opening portion 11.

In the example illustrated in FIG. 4, an arc length of the valve annulus portion 12 from a first commissure portion 13a to a second commissure portion 13b is indicated by reference symbol L1, an arc length of the valve annulus portion 12 from the second commissure portion 13b to a third commissure portion 13c is indicated by reference symbol L2, and an arc length of the valve annulus portion 12 from the third commissure portion 13c to the first commissure portion 13a is indicated by reference symbol L3. Here, all the arc lengths L1, L2, and L3 may be the same. However, it is preferable that at least one arc length is different from the other arc lengths. In particular, it is preferable that all the arc lengths L1, L2, and L3 are different from one another. For example, in the example illustrated in FIG. 4, a relationship of L1>L2>L3 is established. A difference between the arc lengths is preferable to be 1 mm or more, and the difference may be 1.5 mm or more, or 2 mm or more.

Figure 5:
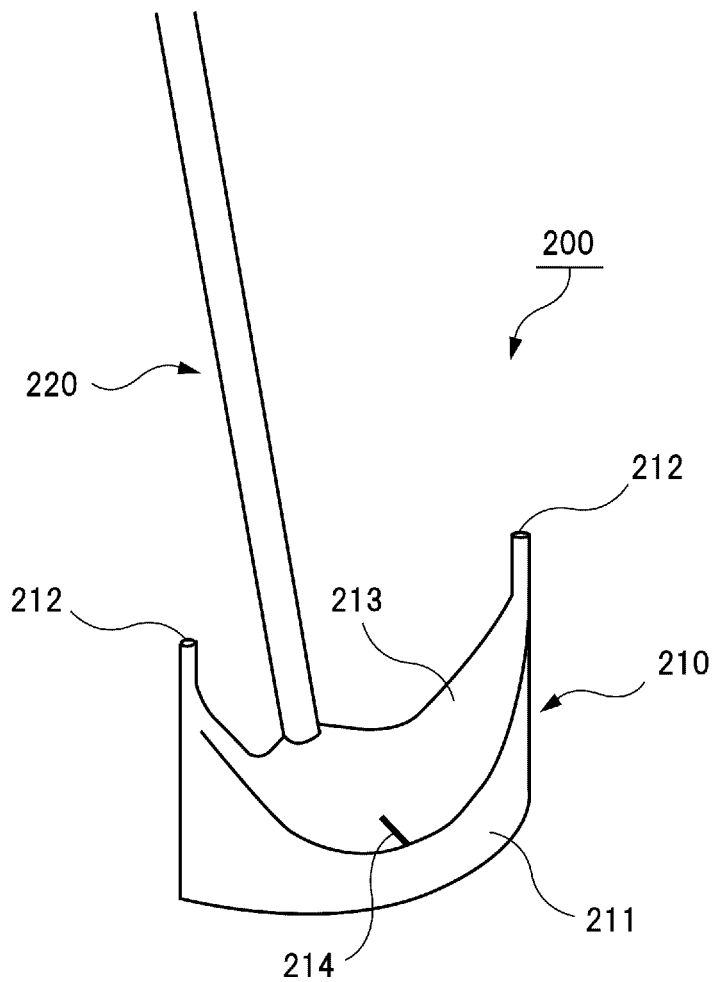
FIG. 5 is a schematic diagram illustrating a valve leaflet sizer.

The arc length between the commissure portions 13 is measured by a valve leaflet sizer 200. An example of the valve leaflet sizer 200 is illustrated in FIG. 5. As illustrated in FIG. 5, for example, the valve leaflet sizer 200 includes a sizer block 210 having an arc surface 211 and a handle 220 which is attached to the sizer block 210 and held by an operator. The sizer block 210 has the arc surface 211 for measuring an arch length of the valve annulus portion 12 from a certain commissure portion 13 to a commissure portion 13 adjacent to the certain commissure portion 13. The arch length of the valve annulus portion 12 varies, so that a plurality of valve leaflet sizers, whose sizes (arch lengths) of the arc surface 211 are different from each other, are prepared in advance. The valve leaflet sizer 200 illustrated in FIG. 5 is one type of a plurality of types of the valve leaflet sizers. A probe needle portion 212 that is brought into contact with the commissure portion 13 for positioning is formed at both end portions of the arc surface 211. An upper surface 213 of the sizer block 210 is curvedly formed into a concave surface shape so that the valve annulus portion 12 between the commissure portions 13 can be seen when the probe needle portions 212 are in contact with the commissure portions 13, respectively. Further, on the upper surface 213, an index 214 that is a center marker to determine a center point between the commissure portions 13 is formed at a position corresponding to the center point. Therefore, when using the valve leaflet sizer 200, it is possible to determine the arc length of the valve annulus portion 12 between the commissure portions 13 and also determine the center point between the commissure portions 13.

Here, the arc length between the commissure portions 13 illustrated in FIG. 4 is determined by using the valve leaflet sizer 200 illustrated in FIG. 5. At this time, when all the arc lengths between the commissure portions 13 are the same, chances to practice determining of the arc length by using the valve leaflet sizer 200 become few. Therefore, as illustrated in FIG. 4, by differentiating all the arc lengths L1, L2, and L3 between the commissure portions 13 from each other, it is possible to repeatedly practice determining of the arc length by using the valve leaflet sizer 200.

As illustrated in FIGS. 1 and 3, the blood vessel model 10 has an enlarged diameter portion 14 between the opening portion 11 and the valve annulus portion 12. The enlarged diameter portion 14 is a portion where the inner diameter of the blood vessel model 10 is greater than the inner diameters of the opening portion 11 and the valve annulus portion 12. Specifically, as illustrated in FIG. 1, in the blood vessel model 10, from the opening portion 11 toward a lower portion, there is a portion of which the diameter is the same as that of the opening portion 11 in a certain length of portion, thereafter the inner diameter gradually increases so that the enlarged diameter portion 14 is formed, and thereafter, the diameter gradually decreases from the enlarged diameter portion 14 so that the valve annulus portion 12 is formed. Regarding a portion located below the valve annulus portion 12, the inner diameter gradually increases again. In FIG. 1, the inner diameter (maximum value) of the enlarged diameter portion 14 is indicated by reference symbol φ3. The inner diameter φ3 of the enlarged diameter portion 14 is greater than the inner diameter φ1 of the opening portion 11, and the inner diameter φ1 of the opening portion 11 is greater than the inner diameter φ2 of the valve annulus portion 12 (φ3>φ1>φ2). For example, the inner diameter φ3 of the enlarged diameter portion 14 is preferable to be 110% to 200% or 150% to 190% of the inner diameter φ1 of the opening portion 11. In this way, the enlarged diameter portion 14 is provided between the opening portion 11 and the valve annulus portion 12, so that it is possible to secure a work space for performing work to suture the valve leaflet model 20 to the valve annulus portion 12 by inserting fingers from the opening portion 11. In an actual surgical operation, when a space in front of the valve annulus portion of the aorta is small, an assistant expands the space by using a retractor or the like while an operator performs a suturing operation of a valve leaflet. On the other hand, by forming the enlarged diameter portion 14 in the blood vessel model 10, the assistant who expands the space in front of the valve annulus portion 12 is not required. Therefore, the operator can use the training kit by himself or herself.

As illustrated in FIG. 1, the blood vessel model 10 may include a left coronary artery portion 15 and a right coronary artery portion 16 on its outer wall. The blood vessel model 10 is a model of an aorta, so that it is possible to understandably show positions where the left coronary artery and the right coronary artery are connected to the aorta by providing the left coronary artery portion 15 and the right coronary artery portion 16. For example, as illustrated in FIG. 1, it is preferable to provide the left coronary artery portion 15 and the right coronary artery portion 16 at positions where a height H2 from the left coronary artery portion 15 and the right coronary artery portion 16 to the opening portion 11 is 10 mm to 20 mm or 13 mm to 17 mm (about 15 mm). The left coronary artery portion 15 and the right coronary artery portion 16 need not be formed into a three-dimensional shape as illustrated in FIG. 1. For example, the left coronary artery portion 15 and the right coronary artery portion 16 may be marks that are formed as holes in the outer wall of the blood vessel model 10.

[1-2. Valve Leaflet Model]

Figure 6:
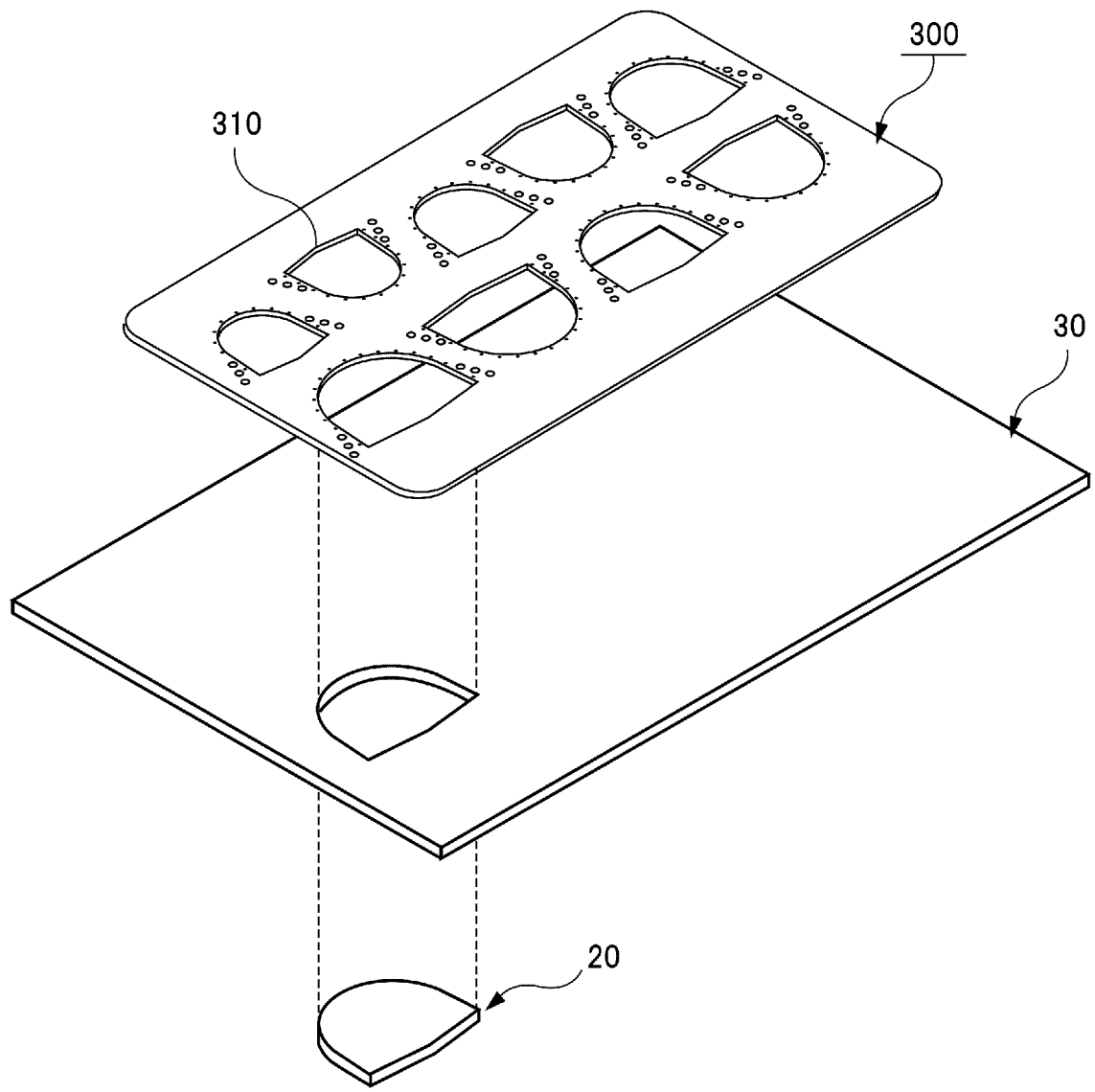
FIG. 6 is a schematic diagram illustrating a state in which a valve leaflet model is cut out from a sheet member by using a template.

Subsequently, the valve leaflet model 20 will be described. FIG. 6 illustrates a sheet member 30 simulating a biological membrane, the valve leaflet model 20 cut out from the sheet member 30, and a template 300 used when cutting out the valve leaflet model 20 from the sheet member 30.

The sheet member 30 can be formed of a flexible material (elastomer) such as silicon, urethane, styrene, synthetic rubber, or natural rubber. In addition, the sheet member 30 may be formed of a flexible material which can maintain its shape and which has elasticity similar to that of living tissue. For example, the sheet member 30 may have a thickness of about 0.5 mm to 1.5 mm, a length of about 8 mm to 9 mm, and a width of about 6 mm to 8 mm.

The template 300 is an auxiliary tool for drawing a valve-leaflet-shaped line on the sheet member 30 according to a size measured by the valve leaflet sizer 200. The template 300 is for drawing a valve-leaflet-shaped line on the sheet member 30 by a surgical skin marker or the like. A plurality of line drawing portions 310, which are valve-leaflet-shaped openings having different sizes, are formed in the template 300. Therefore, it is possible to cut out the valve leaflet model 20 from the sheet member 30 by extending the sheet member 30, pressing the template 300 onto the sheet member 30, drawing a valve-leaflet-shaped line along the line drawing portion 310 by a surgical skin marker or the like, and then cutting the sheet member 30 along the line. As part of the training of an aortic valve reconstruction surgery, the operation described above is performed, in which the arch length of the valve annulus portion 12 between the commissure portions 13 is measured by using the valve leaflet sizer 200 and the valve leaflet model 20 corresponding to the arch length is cut out from the sheet member 30 by using the template 300. Thereafter, as illustrated in FIG. 1 and the like, the valve leaflet model 20 cut out from the sheet member 30 is sutured to the inner wall of the valve annulus portion 12 of the blood vessel model 10. The plurality of valve leaflet models 20 may be cut out from one sheet member 30 or may be cut out from a plurality of sheet members 30.

[1-3. Pedestal]

Subsequently, the pedestal 40 will be described. As illustrated in FIG. 1, the pedestal 40 is attached to a bottom portion side opposite to the opening portion 11 of the blood vessel model 10 and supports the blood vessel model 10 with the opening portion 11 facing up. It is preferable that the pedestal 40 substantially vertically supports the blood vessel model 10. The shape of the pedestal 40 can be appropriately changed. For example, the shape of the pedestal 40 can be cubic, rectangular parallelepiped, cylindrical, truncated square pyramid, or truncated conical. The height H3 of the pedestal 40 may be 70 mm to 150 mm or 80 mm to 120 mm. It is preferable that the height H4 from the bottom surface of the pedestal 40 to the opening portion 11 of the blood vessel model 10 is 150 mm to 350 mm or 200 mm to 300 mm. However, when the blood vessel model 10 stands up independently, the pedestal 40 may not be provided. When the blood vessel model 10 is disposable, the pedestal 40 is not discarded and only the blood vessel model 10 inserted into the pedestal 40 may be replaced.

Further, as illustrated in FIG. 1, in the pedestal 40 or in a cylinder of the blood vessel model 10, a photographing unit 50 may be provided which photographs a state in the cylinder of the blood vessel model 10 in which the valve leaflet model 20 is sutured to the valve annulus portion 12 from the bottom portion side of the blood vessel model 10. The photographing unit 50 is preferable to be a unit that has a function to photograph a moving image, such as a digital camera. A state seen from the bottom portion side of the blood vessel model 10 cannot be visibly recognized by an operator. Therefore, by photographing and recording a suturing operation of the operator from the bottom portion side by the photographing unit 50, it is possible to feed back the state of the suturing operation of the operator to the operator. Thereby, the operator can well understand how to quickly and correctly suture a valve leaflet to the valve annulus portion of the aorta.

[2. Bicuspid Type Training Kit]

Figure 7:
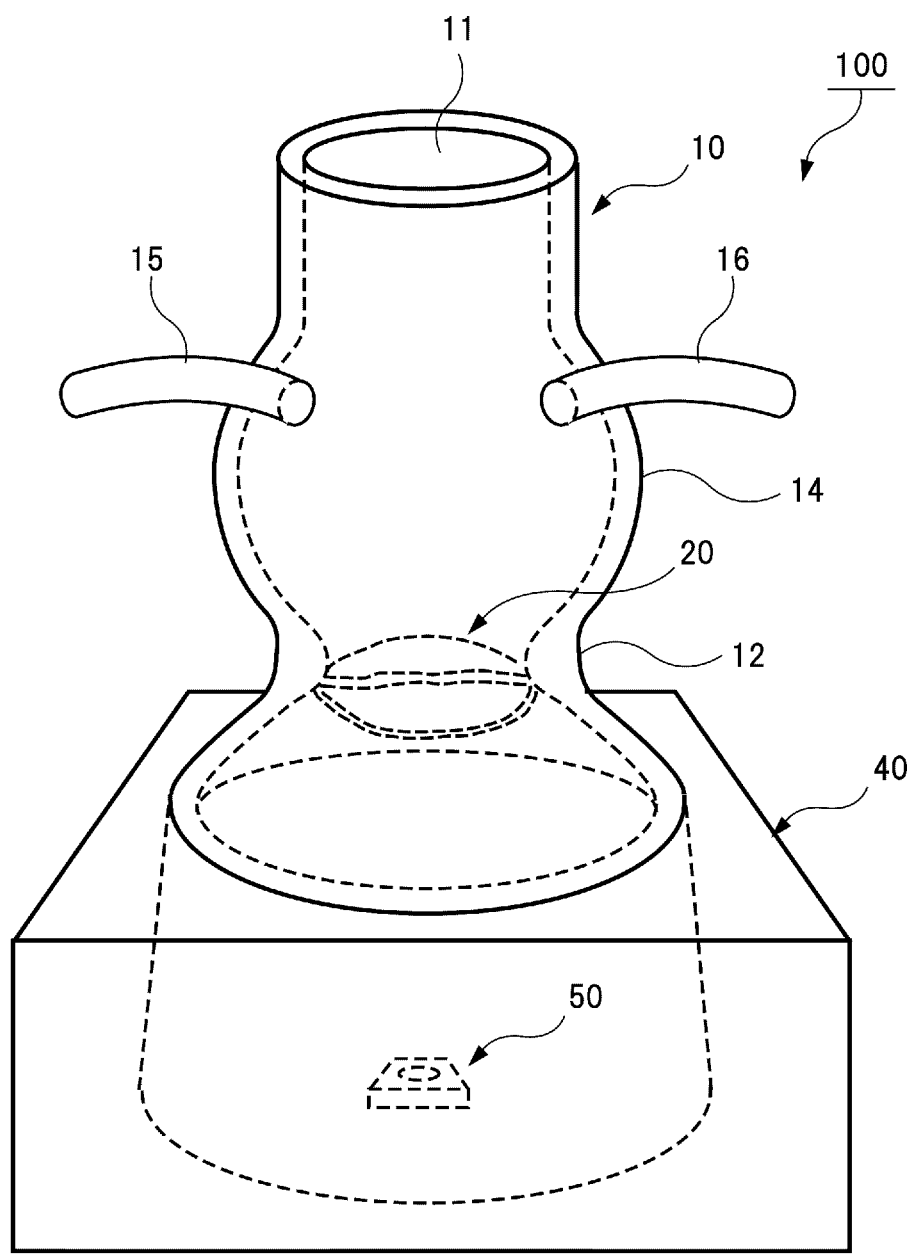
FIG. 7 is a schematic diagram illustrating an entire configuration of a training kit for a bicuspid type heart valve.
Figure 8:
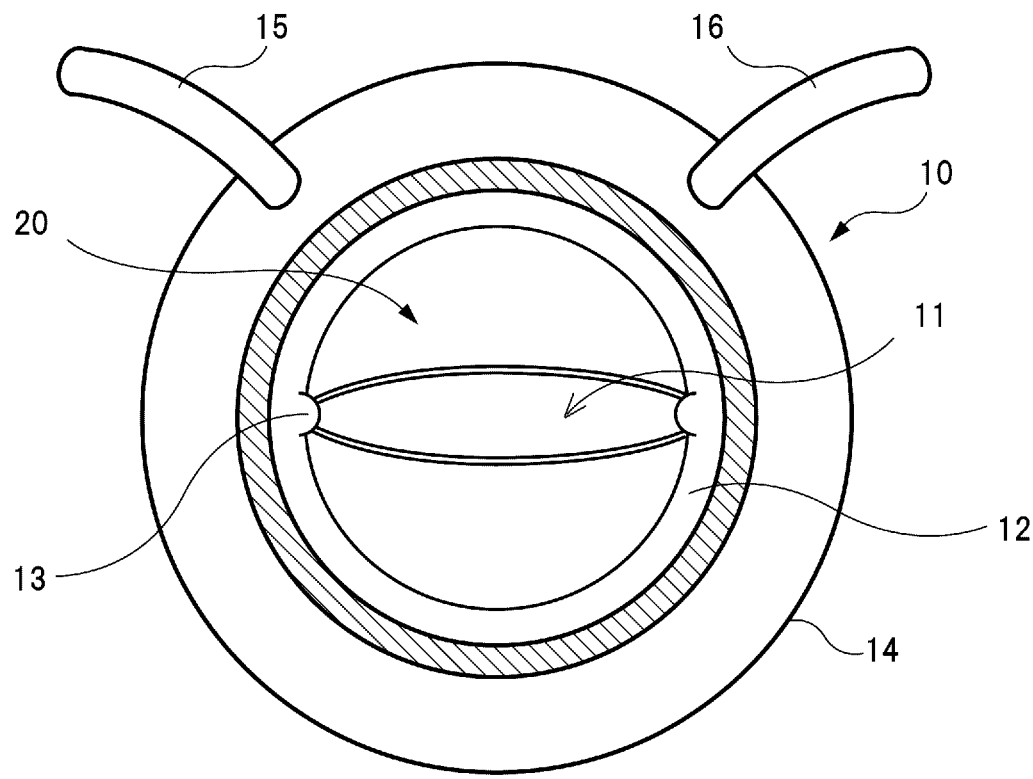
FIG. 8 is a plan view illustrating a blood vessel model as viewed from an upper opening portion.
Figure 8:
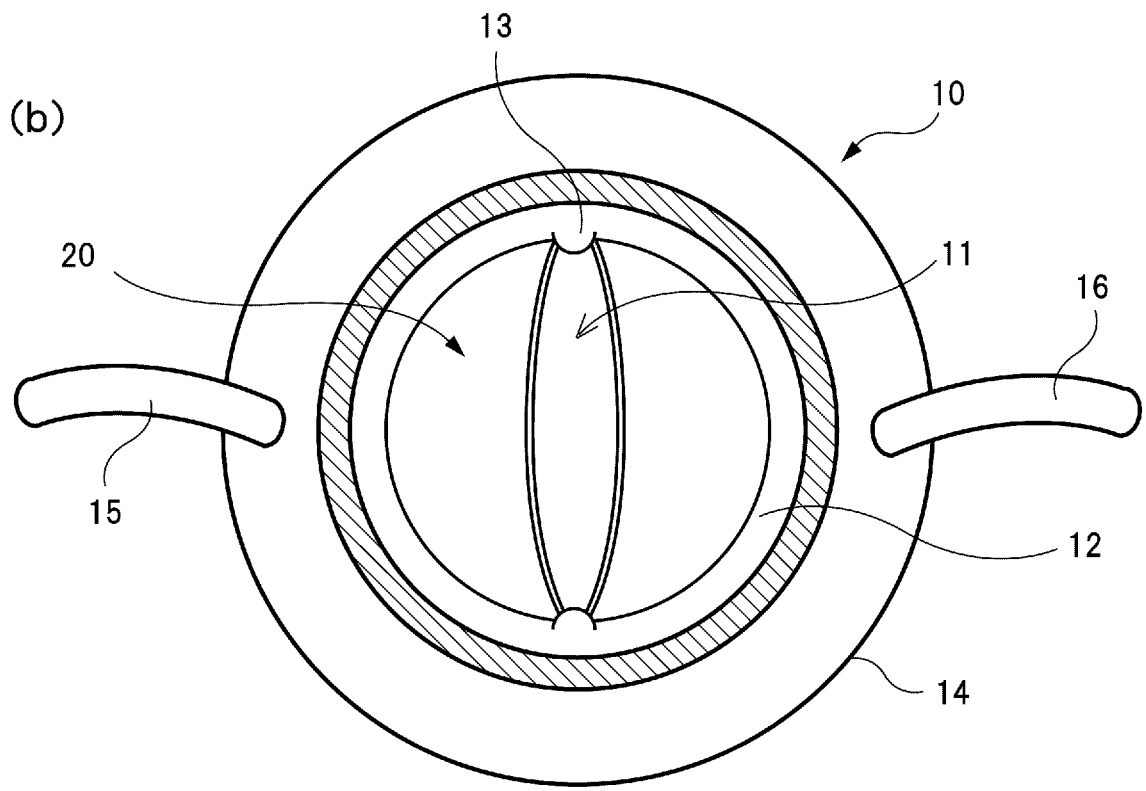
Figure 9:
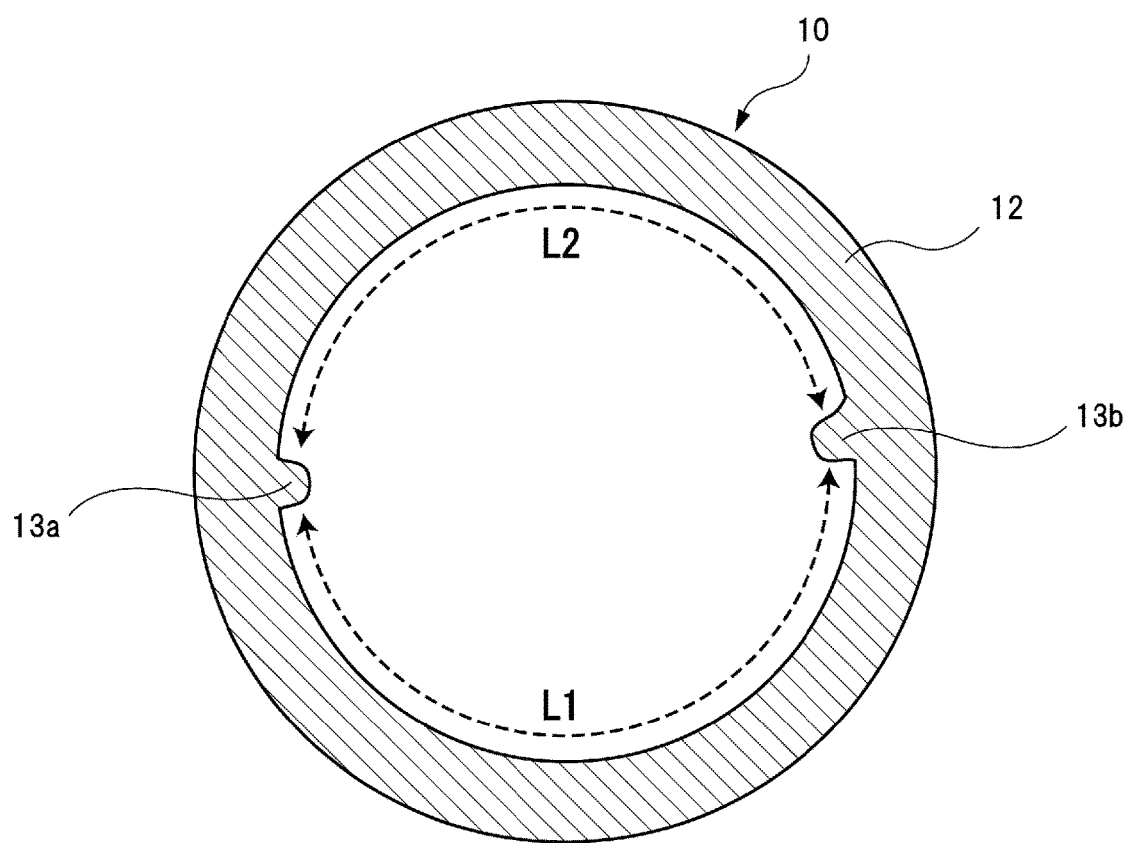
FIG. 9 is a cross-sectional view illustrating a structure of a valve annulus portion of the blood vessel model.

FIGS. 7 to 9 illustrate a training kit 100 for a bicuspid type aortic valve reconstruction surgery. The bicuspid type training kit has basically the same structure as that of the tricuspid type training kit illustrated in FIGS. 1 to 6. However, the bicuspid type training kit is different from the tricuspid type training kit in that the number of the valve leaflet models 20 to be sutured to the valve annulus portion 12 of the blood vessel model 10 is two and the number of the commissure portions 13 formed on the valve annulus portion 12 is two. The number of valve leaflets formed between the left ventricle of the heart and the aorta may be three or two depending on a patient. Therefore, it is preferable to prepare a tricuspid type training kit 100 and a bicuspid type training kit 100.

In the case of a bicuspid type aorta, there are a front-rear type in which positions of inlet ports of the left and right coronary artery portions 15 and 16 are located at positions of about two o'clock and ten o'clock as illustrated in FIG. 8(a) and a left-right type in which positions of inlet ports of the left and right coronary artery portions 15 and 16 are located at positions of about three o'clock and nine o'clock (horizontal position) as illustrated in FIG. 8(b). To be able to practice both the front-rear type and the left-right type, it is preferable to prepare both types of the training kits.

As illustrated in FIG. 9, in the bicuspid type training kit, the two commissure portions 13 formed on the valve annulus portion 12 of the blood vessel model 10 may be formed so that the arc length L1 of the valve annulus portion 12 between the commissure portions 13 when being measured in a counterclockwise direction is different from the arc length L2 of the valve annulus portion 12 between the commissure portions 13 when being measured in a clockwise direction. Thereby, it is possible to increase the number of times of training for determining the arch length of the valve annulus portion 12 by using the valve leaflet sizer 200. However, the arc length L1 and the arc length L2 can be the same length.

Occasionally there is a patient who has four valve leaflets between the ventricle and the aorta, so that it is possible to manufacture a quadricuspid type training kit. Further, occasionally there may be actually a unicuspid type training kit.

[3. Fixing Base]

Figure 10:
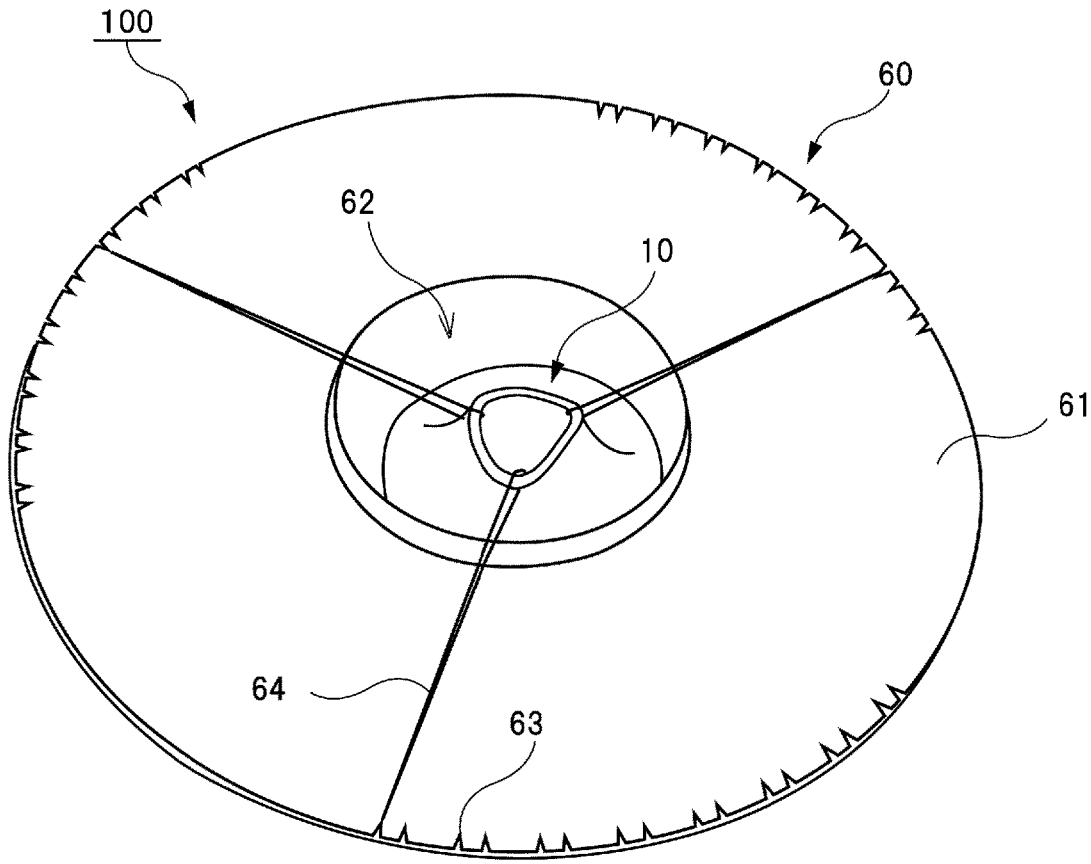
FIG. 10 is a perspective view illustrating a training kit according to another embodiment.

FIG. 10 illustrates a training kit 100 according to another embodiment. As illustrated in FIG. 10, the training kit 100 further includes a fixing base 60. The fixing base 60 has a disk-shaped plate 61. A housing hole 62 is formed in a central portion of the plate 61, and the blood vessel model 10 can be housed in the housing hole 62. A plurality of notches 63 are formed on a peripheral edge of the disk-shaped plate 61. The plurality of notches 63 may be formed over the entire peripheral edge of the disk-shaped plate 61. As illustrated in FIG. 10, a plurality of notches 63 may be formed in each of three regions located in three directions on the peripheral edge of the disk-shaped plate 61. Further, a thread member 64 that is sutured near the upper opening portion of the blood vessel model 10 is hooked in the notch 63. In other words, one end of the thread member 64 is sutured to an upper portion of the blood vessel model 10 and the other end is hooked in the notch 63 of the plate 61. For example, it is preferable to prepare two, three or more thread members 64.

By doing so, it is possible for the thread members 64 to pull the opening portion of the blood vessel model 10 so as to open the opening portion. Further, by shifting the thread members 64 and changing the notches 63 where the thread members 64 are hooked, it is possible to change angles at which the blood vessel model 10 is pulled. Thereby, it is possible to finely adjust directions to which the opening portion of the blood vessel model 10 is opened, so that it is possible to secure a visual field for looking into the inside of the opening portion of the blood vessel model 10 from various angles. In this way, it is possible to install the fixing base 60 for fixing the blood vessel model 10 in the training kit 100.

In the description of the present application, the embodiments of the present invention are described with reference to the drawings in order to represent content of the present invention. However, the present invention is not limited to the embodiments described above and includes modified embodiments and improved embodiments that are obvious to those skilled in the art based on the matters stated in the description of the present application.

INDUSTRIAL APPLICABILITY

The present invention relates to a training kit that can be used for practice of the aortic valve reconstruction surgery. The present invention can be suitably used in a medical field.

REFERENCE SIGNS LIST 10 blood vessel model
11 opening portion
12 valve annulus portion
13 commissure portion
14 enlarged diameter portion
15 left coronary artery portion
16 right coronary artery portion
20 valve leaflet model
30 sheet member
40 pedestal
50 photographing unit
60 fixing base
61 plate
62 housing hole
63 notch
64 thread member
100 training kit
200 valve leaflet sizer
210 sizer block
211 arc surface
212 probe needle portion
213 upper surface
214 index
220 handle
300 template
310 line drawing portion

The invention claimed is:

1. A training kit for an aortic valve reconstruction surgery, the training kit comprising:
a blood vessel model; and
a plurality of valve leaflet models or a sheet from which the plurality of valve leaflet models are cut out,
wherein the blood vessel model comprises:
a bottomed cylindrical shape or a bottomless cylindrical shape where an opening is formed at least at an upper portion thereof, and
a valve annulus, to which the valve leaflet model can be sutured, at around middle of the cylindrical shape,
wherein the training kit further comprises:
a disk-shaped plate which is configured to have a housing hole, the blood vessel model being inside the housing hole, and a plurality of notches on the peripheral edge thereof; and a plurality of threads, wherein one end of each of the plurality of thread is sutured to an upper portion of the blood vessel model and the other end is hooked at one of the notches.

2. The training kit according to claim 1, wherein the valve annulus is formed thick over an entire circumference thereof so as to protrude into the blood vessel model.

3. The training kit according to claim 1, wherein the valve annulus comprises a plurality of commissures formed at intervals in a circumferential direction of the blood vessel model, and the plurality of commissures is provided distinguishably from the other regions in the valve annulus.

4. The training kit according to claim 3, wherein arc lengths of the valve annulus between the plurality of commissures are set to be different from each other.

5. The training kit according to claim 1, wherein the blood vessel model further includes an enlarged diameter between the opening and the valve annulus, the enlarged diameter having an inner diameter greater than inner diameters of the opening and the valve annulus.

6. The training kit according to claim 1, further comprising a pedestal for supporting the blood vessel model with the opening facing up on a bottom side opposite to the opening of the blood vessel model.

7. The training kit according to claim 1, wherein the plurality of notches is formed over an entire peripheral edge of the disk-shaped plate.

8. The training kit according to claim 1, wherein a plurality of notches is formed in each of three regions located in three directions on the peripheral edge of the disk-shaped plate.

* * * * *